(12) United States Patent
Virkus et al.

(10) Patent No.: US 11,504,171 B2
(45) Date of Patent: Nov. 22, 2022

(54) INTRAMEDULLARY ROD WITH INTRABODY OUTRIGGER INTERFACE

(71) Applicant: GLW, Inc., Waxhaw, NC (US)

(72) Inventors: Walter Warren Virkus, Zionsville, IN (US); Axel Cremer, Fahrenkrug (DE)

(73) Assignee: GLW, Inc., Englewood Cliffs, NJ (US)

( * ) Notice: Subject to any disclaimer, the term of this patent is extended or adjusted under 35 U.S.C. 154(b) by 13 days.

(21) Appl. No.: 16/937,021

(22) Filed: Jul. 23, 2020

(65) Prior Publication Data

US 2021/0022780 A1 Jan. 28, 2021

Related U.S. Application Data

(60) Provisional application No. 62/879,213, filed on Jul. 26, 2019.

(51) Int. Cl.
*A61B 17/72* (2006.01)
(52) U.S. Cl.
CPC ................ *A61B 17/7241* (2013.01)
(58) Field of Classification Search
CPC .......................................... A61B 17/72–7291
See application file for complete search history.

(56) References Cited

U.S. PATENT DOCUMENTS

| | | |
|---|---|---|
| 4,913,137 A | 4/1990 | Azer et al. |
| 5,122,141 A * | 6/1992 | Simpson ............... A61B 17/72 606/62 |
| 5,375,956 A | 12/1994 | Pennig |
| 5,403,321 A | 4/1995 | DiMarco |
| 5,478,341 A | 12/1995 | Cook et al. |
| 5,505,734 A * | 4/1996 | Caniggia ............ A61B 17/7225 606/63 |
| 5,620,449 A | 4/1997 | Faccioli et al. |

(Continued)

FOREIGN PATENT DOCUMENTS

WO 9739693 A1 10/1997

OTHER PUBLICATIONS

PCT Search Report and Written Opinion, Application No. PCT/US2020/043260, dated Nov. 3, 2020.

*Primary Examiner* — Eduardo C Robert
*Assistant Examiner* — Steven J Cotroneo
(74) *Attorney, Agent, or Firm* — MacMillan, Sobanski & Todd, LLC

(57) ABSTRACT

Intramedullary rods, targeting devices, intramedullary rod systems, intramedullary rod kits, and methods of placing an intramedullary rod in a bone are described. An intramedullary rod comprises a head member having a first end, a second end, and a body extending between the first end of the head member and the second end of the head member. The head member is formed of a first material and defines a circumferential flange and a circumferential shoulder. The circumferential flange extends radially outwardly from the head member and the circumferential shoulder is disposed between the first end of the head member and the circumferential flange. A shaft member extends from the head member and a head extension is partially disposed over the head, member. The head extension is formed of a second material that is different than the first material and has an end contacting the circumferential shoulder of the head member.

20 Claims, 10 Drawing Sheets

(56) References Cited

U.S. PATENT DOCUMENTS

| | | | |
|---|---|---|---|
| 5,658,287 A * | 8/1997 | Hofmann | A61B 17/72 606/63 |
| 5,855,579 A * | 1/1999 | James | A61B 17/72 606/328 |
| 6,027,506 A | 2/2000 | Faccioli et al. | |
| 6,039,739 A | 3/2000 | Simon | |
| 6,126,661 A | 10/2000 | Faccioli et al. | |
| 6,183,477 B1 | 2/2001 | Pepper | |
| 6,702,823 B2 | 3/2004 | Taia | |
| 7,041,104 B1 * | 5/2006 | Cole | A61B 17/72 606/62 |
| 7,077,847 B2 | 7/2006 | Pusnik et al. | |
| 7,144,399 B2 | 12/2006 | Hayes et al. | |
| 7,175,631 B2 | 2/2007 | Wilson et al. | |
| 7,608,075 B2 * | 10/2009 | Tornier | A61B 17/72 606/64 |
| 7,763,021 B2 * | 7/2010 | Cole | A61B 17/7241 606/64 |
| 8,025,666 B2 | 9/2011 | Roth et al. | |
| 8,128,627 B2 * | 3/2012 | Justin | A61B 17/7266 606/62 |
| 8,182,490 B2 | 5/2012 | Christie | |
| 8,328,807 B2 | 12/2012 | Brigido | |
| 8,591,517 B2 | 11/2013 | Metzinger et al. | |
| 8,795,287 B2 | 8/2014 | Fritzinger et al. | |
| 8,911,446 B2 | 12/2014 | Thornes et al. | |
| 9,155,582 B2 | 10/2015 | Felder et al. | |
| 9,173,664 B2 | 11/2015 | Metzinger et al. | |
| 9,320,555 B2 * | 4/2016 | Probe | A61B 17/8685 |
| 9,532,817 B2 | 1/2017 | Overes | |
| 10,039,606 B2 | 8/2018 | Blau et al. | |
| 2002/0133172 A1 | 9/2002 | Lambrecht et al. | |
| 2002/0151898 A1 * | 10/2002 | Sohngen | A61B 17/7233 606/62 |
| 2003/0204268 A1 | 10/2003 | Gerbec et al. | |
| 2006/0064106 A1 | 3/2006 | Fernandez | |
| 2008/0027559 A1 | 1/2008 | Crowninshield et al. | |
| 2011/0054484 A1 | 3/2011 | Brandon | |
| 2011/0184477 A1 | 7/2011 | Dell'Oca et al. | |
| 2013/0325007 A1 * | 12/2013 | Beyar | A61B 17/7208 606/62 |
| 2015/0374411 A1 * | 12/2015 | Ehmke | A61B 17/7233 606/329 |
| 2017/0007303 A1 | 1/2017 | Hansson | |
| 2017/0079699 A1 | 3/2017 | Fallin et al. | |
| 2017/0100182 A1 | 4/2017 | Shah et al. | |
| 2017/0105776 A1 * | 4/2017 | Lutz | A61B 17/72 |
| 2017/0112552 A1 * | 4/2017 | Sinnott | A61B 17/7233 |
| 2017/0143391 A1 * | 5/2017 | Jansen | A61B 17/7275 |
| 2017/0164992 A1 | 6/2017 | Dassonville et al. | |
| 2018/0344377 A1 | 12/2018 | Mcmanus | |
| 2019/0038326 A1 | 2/2019 | Hedgeland et al. | |
| 2019/0053836 A1 * | 2/2019 | Sweeney | A61B 17/72 |
| 2019/0216513 A1 * | 7/2019 | Sands | A61B 17/72 |
| 2021/0251661 A1 * | 8/2021 | Kay | A61B 17/68 |

* cited by examiner

INTRAMEDULLARY ROD WITH INTRABODY OUTRIGGER INTERFACE

CROSS REFERENCE TO RELATED APPLICATION

This application claims the benefit of U.S. Provisional Application No. 62/879,213, filed on Jul. 26, 2019, which is hereby incorporated by reference into this disclosure in its entirety.

FIELD

The disclosure relates to the field of medical devices. More particularly, the disclosure relates to intramedullary rods useful in the repair of fractured bones. The disclosure also relates to targeting devices for use with the intramedullary rods during orthopedic procedures, intramedullary rod systems, intramedullary rod kits, and methods of placing an intramedullary rod in a bone.

BACKGROUND

Intramedullary rods, also referred to as intramedullary nails or bone nails, are implantable medical devices that are commonly used for fracture stabilization and fixation. Intramedullary rods are often cannulated to allow them to be placed over a wire to guide their positioning and to align bone fragments sought to be stabilized. Rods often include structural features, such as through passageways, to facilitate placement of locking screws used to attach parts of the fractured bone to die nail or to ensure a reliable fixation of the rod in the intramedullary canal.

A targeting device, also referred to as an outrigger, is attached to the intramedullary rod during placement to facilitate precise positioning of locking screws through the accommodating structural features in the rod. The structural interface between the targeting device and the intramedullary rod is critical for the function of the system and achievement of a desired positioning of the rod and associated locking screws. The interface needs to be precise but also must be able to transmit high torsional moments, high bending moments and high impact forces during rod insertion, adjustment and nail removal. This is particularly critical during placement of the intramedullary rod, which often involves use of a hammer to transmit force onto the rod.

Conventional targeting devices attach to the topmost surface of the intramedullary rod to form the structural interface between the targeting device and intramedullary rod. Unfortunately, this structural arrangement places limitations on the design of intramedullary rods.

A need remains, therefore, for improved intramedullary rods, targeting devices for use with the intramedullary rods during orthopedic procedures, intramedullary rod systems, intramedullary rod kits, and methods of placing an intramedullary rod in a bone.

BRIEF SUMMARY OF SELECTED EXAMPLES

Various example intramedullary rods are described.

An example intramedullary rod comprises a head member having a first end, a second end, and a body extending between the first end of the head member and the second end of the head member, the head member formed of a first material and defining a circumferential flange and a circumferential shoulder, the circumferential flange extending radially outwardly from the head member and lying on a plane extending through the longitudinal axis of said intramedullary rod, the circumferential shoulder disposed between the first end of the head member and the circumferential flange; a shaft member extending the head member, the shaft member having a first end, a second end, and a body extending between the first end of the shaft member and the second end of the shaft member; and a head extension partially disposed over the head member and having a first end, a second end, a wall, the head extension formed of a second material that is different than the first material, the second end of the head extension contacting the circumferential shoulder of the head member.

Another example intramedullary rod comprises ahead member having a first end, a second end, and a body extending between the first end of the head member and the second end of the head member, the head member formed of a first material and defining a circumferential flange and a circumferential shoulder, the circumferential flange extending radially outwardly from the head member and lying on a plane extending through the longitudinal axis of said intramedullary rod, the circumferential shoulder disposed between the first end of the head member and the circumferential flange, the head member further defining a first opening, a second opening, and a passageway extending through the head member from the first opening to the second opening; a shaft member extending the head member; the shaft member having a first end, a second end, and a body extending between the first end of the shaft member and the second end of the shaft member; a head extension partially disposed over the head member and having a first end, a second end, a wall, the head extension formed of a second material that is different than the first material, the second end of the head extension contacting the circumferential shoulder of the head member; and an outer body member disposed circumferentially about the shaft member and a portion of the head member, a portion of the outer body member disposed around the first opening of the head member.

Another example intramedullary rod comprises a head member having a first end, a second end, and a body extending between the first end of the head member and the second end of the head member, the head member formed of a first material and defining a circumferential flange and a circumferential shoulder, the circumferential flange extending radially outwardly from the head member and, lying on a plane extending through the longitudinal axis of said intramedullary rod, the circumferential shoulder disposed between the first end of the head member and the circumferential flange, the head member further defining a first opening, a second opening, and, a passageway extending through the head member from the first opening to the second opening; a shaft member extending the head member, the shaft member having a first end, a second end, and a body extending between the first end of the shaft member and the second end of the shaft member; a head extension partially disposed over the head member and having a first end, a second end, a wall, the head extension formed of a second material that is different than the first material, the second end of the head extension contacting, the circumferential shoulder of the head member; and an outer body member disposed circumferentially about the shaft member and a portion of the head member, a portion of the outer body member disposed around the first opening of the head member. Each of the head member and the shaft member comprises a metal and each of the head extension and outer body member comprises a radiolucent material.

Various example intramedullary rod systems are described.

An example intramedullary rod system comprises an intramedullary rod comprising a head member having a first end, a second end, and a body extending between the first end of the head member and the second end of the head member, the head member formed of a first material and defining a circumferential flange and a circumferential shoulder, the circumferential flange extending radially outwardly from the head member and lying on a plane extending through the longitudinal axis of said intramedullary rod, the circumferential shoulder disposed between, the first end of the head member and the circumferential flange; a shaft member extending the head member, the shaft member having a first end, a second end, and a body extending between the first end of the shaft, member and the second end of the shaft member; and a head extension partially disposed over the head member and having a first end, a second end, a wall, the head extension formed of a second material that is different than the first material, the second end of the head extension contacting the circumferential shoulder of the head member. The intramedullary rod is removably attached to a targeting device having a terminal rod contacting surface such that the terminal rod contacting surface of the targeting device is in contact interface with the circumferential shoulder of the intramedullary rod.

Various intramedullary rod kits are described.

An example intramedullary rod kit comprises a least one intramedullary rod comprising a head member having a first end, a second end, and a body extending between the first end of the head member and the second end of the head member, the head member formed of a first material and defining a circumferential flange and a circumferential shoulder, the circumferential flange extending radially outwardly from the head member and lying on a plane extending through the longitudinal axis of said intramedullary rod, the circumferential shoulder disposed between the first end of the head member and the circumferential flange; a shaft member extending the head member, the shaft member having a first end, a second end, and a body extending between the first end of the shaft member and the second end of the shaft member; and a head extension partially disposed over the head member and having a first end, a second end, a wall, the head extension formed of a second material that is different than the first material, the second end of the head extension contacting the circumferential shoulder of the head member. The intramedullary rod kit further comprises a targeting device having a terminal rod contacting surface such that, the terminal rod contacting surface of the targeting device is in contact interface with the circumferential shoulder of the intramedullary rod.

Various example methods of placing an intramedullary rod in a bone are described.

An example method of placing an intramedullary rod in a bone comprises removably attaching an intramedullary rod according to an embodiment to a targeting device having a terminal rod contacting surface such that the terminal rod contacting surface of the targeting device is in contact interface with the circumferential shoulder of the intramedullary rod; inserting the intramedullary rod into the intramedullary canal of said bone; applying force to the targeting device such that the force is transferred onto the circumferential shoulder of the intramedullary rod and the intramedullary rod is advanced in, the intramedullary canal of said bone; securing the intramedullary rod to said bone; and removing the targeting device from contact interface with the intramedullary rod.

Additional understanding of the inventive intramedullary rods, targeting devices, intramedullary rod systems, intramedullary rod kits, and methods of placing an intramedullary rod in a bone can be obtained by reviewing the detailed description of selected examples, below, with reference to the appended drawings.

DETAILED DESCRIPTION OF SELECTED EXAMPLES

The following detailed description and the appended drawings describe and illustrate various example intramedullary rods, targeting devices, intramedullary rod systems, intramedullary rod kits, and methods of placing an intramedullary rod in a bone. The description and illustration of these examples enable one skilled in the art to make and use examples, of the inventive intramedullary rods, targeting devices, intramedullary rod systems, and intramedullary rod kits, and to perform examples of the inventive methods of placing an intramedullary rod in a bone. They do not limit the scope of the claims in any manner.

As used herein, the term "lumen," and grammatically related terms, refers to the inside space of a tubular structure. The term does not require any specific dimensions, relative dimensions, configuration, or regularity.

As used herein, the term "outrigger," and grammatically related terms, refers to a targeting device used with an intramedullary rod in the placement of the intramedullary rod in a bone.

As used herein, the term "circumferential," and grammatically related terms, refers to a structural arrangement of one structure relative to another structure, feature, or property of another structure. The term does not require any specific dimensions, relative dimensions, configuration, or regularity of either structure.

Figure 1:
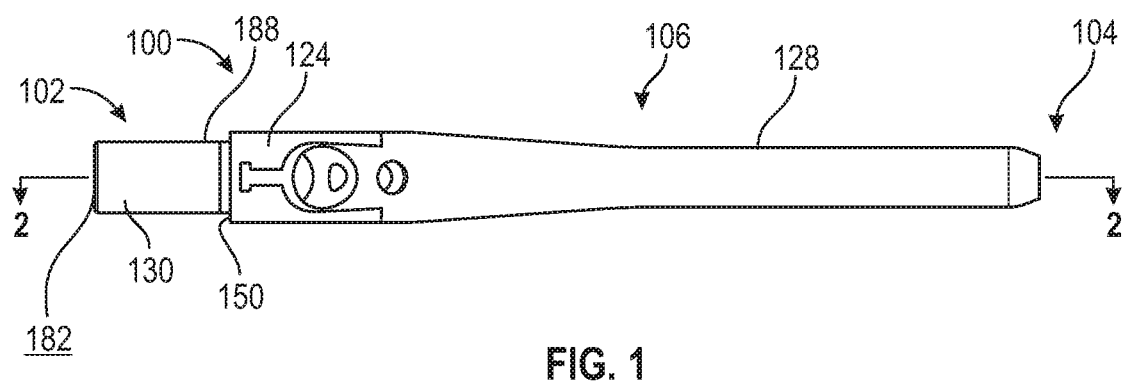
FIG. 1 is a side view of an example intramedullary rod.
Figure 2:
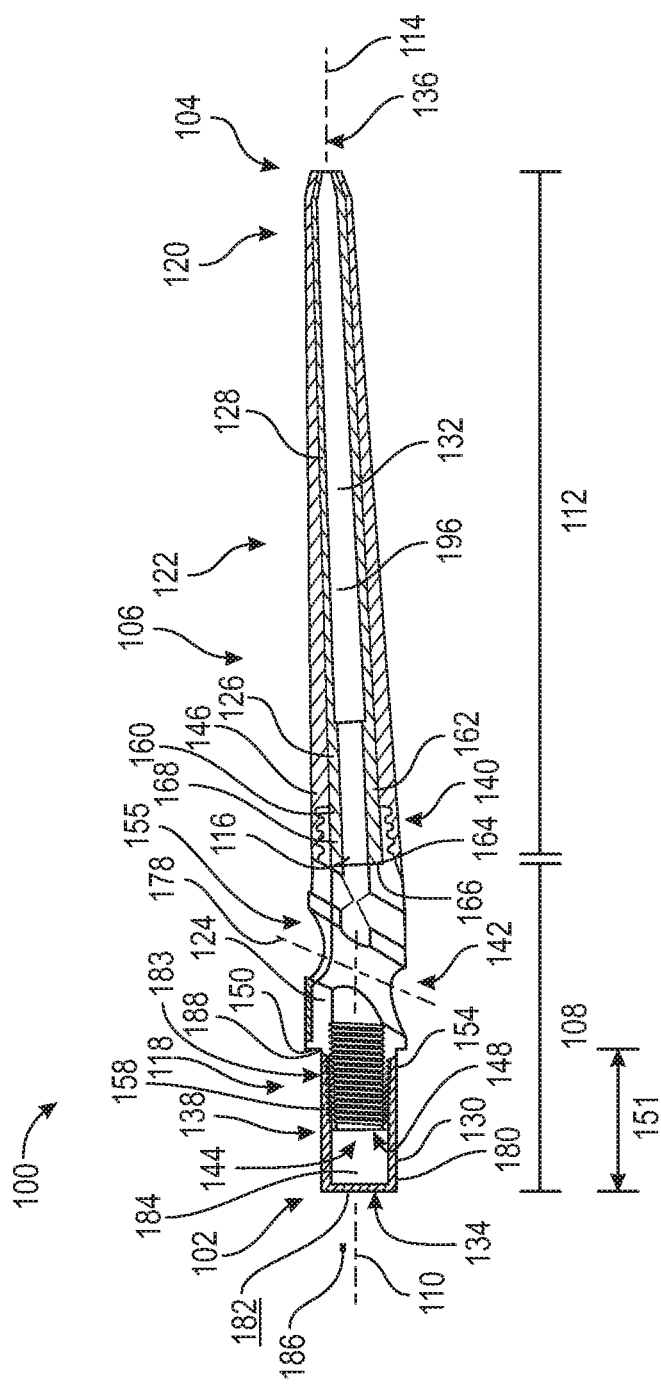
FIG. 2 is sectional view of the intramedullary rod illustrated in FIG. 1, taken along line 2-2 in FIG. 1.

FIGS. 1 and 2 illustrate a first example intramedullary rod 100. FIG. illustrates the first example intramedullary rod 100 with an attached cap 200. The intramedullary rod 100 has a first end 102, a second end 104, and a body 106 extending between the first end 102 and the second end 104. A first portion 108 of the intramedullary rod 100 extends along a first longitudinal axis 110, and a second portion 112 of the intramedullary rod 100 extends along a second, longitudinal axis 114. In the illustrated example, the first 110 and second 114 longitudinal axes intersect at a non-linear angle 116. The intramedullary rod 100 includes a head portion 118 that, includes the first end 102, a tip portion 120 that includes the second end 104, and a shaft portion 122 extending between the head portion 118 and the tip portion 120 and comprising the body 106. Also, the intramedullary rod 100 includes a head member 124, a shaft member 126 partially disposed within the head member 124, and an outer body member 128 disposed circumferentially around the shaft member 126 and a portion of the head member 124. A head extension 130 is disposed on a portion of the head member 124 and extends away from the second end 104 of the intramedullary rod 100 to the first end 102 of the intramedullary rod 100. A device lumen 132 extends through the entire axial length of the intramedullary rod 100 from a first opening 134 defined at the first end 102 of the intramedullary rod 100 by the head extension 130 to a second opening 136 defined at the second end 104 of the intramedullary rod 100 by the shaft member 126, placing the entire device lumen 132 in communication with the environment external to the intramedullary rod 100. As such, the intramedullary rod 100 is a cannulated rod, allowing it to be passed over a separate member, such as a wire, to facilitate placement and/or positioning during implantation.

The head, portion 118 provides structure for receiving a bone screw, such as a locking or lag screw commonly used in the stabilization and fixation of bone fractures, such as hip fractures. For example, the head portion 118 includes the head member 124, which defines a passageway for receiving a screw, as described in detail below. Also, the head portion 118 provides structure for interfacing with a targeting device, such as a targeting device according to an embodiment described herein. For example, the head portion 118 includes the head extension 130, which cooperates with the head member 124 to interface with a targeting device, as described in detail below. The tip portion 120 provides structure for interfacing with the medullary canal of a bone, such as a femur, during placement, as well as structure for receiving distal locking screws commonly used in the stabilization and fixation of bone fractures, such as hip fractures.

The head member 124 has a first end 138, a second end 140, and a body 142 extending between the first end 138 and the second end 140. The first end 138 defines a first opening 144 and the second end 140 defines a second opening 146. As best illustrated in FIG. 2, the head member 124 defines a head member lumen 148 extending between the first opening 144 and the second opening 146. In the assembled intramedullary rod 100, the first opening 144 provides access to the head member lumen 148 from the head extension lumen 184 and the second opening 146 receives a portion of the shaft member 126 in a manner that positions the head member lumen 148 in line with the shaft member lumen 196 defined by the shaft member 126. In use, the intramedullary rod 100 can be passed over a previously-placed wire such that the wire extends through the shaft member 126, the head member lumen 148 and, ultimately, through the head extension lumen 184 if desired or necessary. In this manner, the intramedullary rod 100 can then be advanced over the wire to a desired degree to achieve a desired placement and/or positioning before securing the intramedullary rod 100 within the medullary canal.

Figure 5:
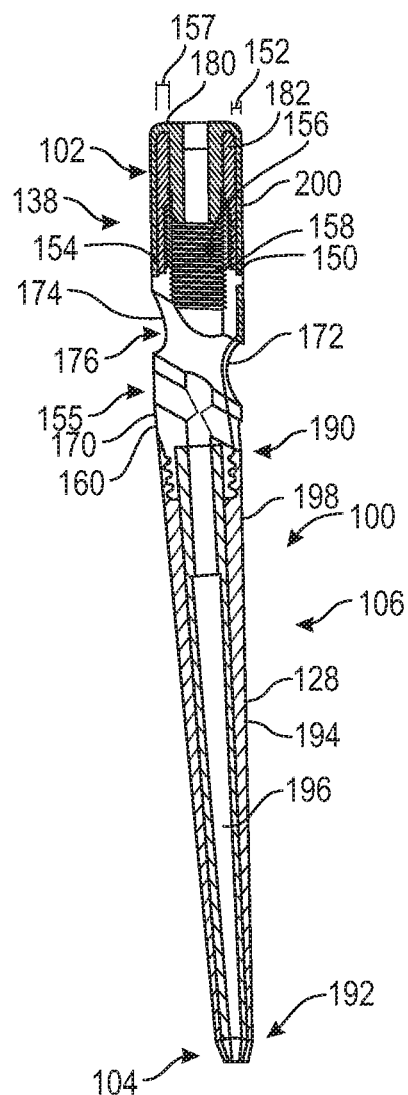
FIG. 5 is a sectional view of the intramedullary rod illustrated in FIG. 1 with the cap illustrated in FIG. 3 attached to the intramedullary rod.

The first end 138 of the head member 124 defines a circumferential flange 150 that extends radially outwardly from the head member 124 and lies on a plane that is orthogonal to the first longitudinal axis 110 of the intramedullary rod 100. As best illustrated in FIG. 5, the circumferential flange 150 defines a stop for cap 200 when disposed on the intramedullary rod 100 and is disposed a distance 151 from the terminal surface 182 of the head extension 130, as described in more detail herein. Also, as described, in detail below, the circumferential flange 150 provides a surface for forming a contact interface with a targeting device. Also as best illustrated in FIG. 5, the circumferential flange 150 has a radial width 152 that is equal to, or substantially the same as, the wall width 214 of the cap 200. Also as described in detail below, the radial width 152 is equal to, or substantially the same as, a wall width of a rod engaging sleeve (e.g., rod engaging sleeve 418) of a targeting device intended for use with the intramedullary rod 100. The head member 124 also defines a circumferential shoulder 154 and passageway 156 bounded by threaded wall 158. As best illustrated in FIG. 5, circumferential shoulder 154 is disposed between the first end 138 of the head member 124 and the circumferential flange 150 and is radially inward of the circumferential flange 150. Also as best illustrated in FIG. 5, the circumferential shoulder 154, passageway 156, and the threaded wall 158 cooperate to provide structure for forming an interface with cap 200 and, as described in detail below, with a targeting device intended to be used with intramedullary rod 100.

The second end 140 of the head member 124 forms an extension 160 that defines a cavity 162 bounded by a circumferential wall 164 and a transverse wall 166. The circumferential wall 164 surrounds the second longitudinal axis 114 of the intramedullary rod 100. The circumferential wall 164 defines structure that facilitates formation of an interface 168 between the head member 124 and the shaft member 126. The transverse wall 166 may also define structure that facilitates such interaction. As such, the circumferential wall 164, the transverse wall 166, and, as a result, the cavity 162 may have any suitable configuration and a skilled artisan will be able to select an appropriate configuration for each of these structures in an intramedullary rod according to a particular embodiment based on various considerations, including the configuration and nature of the shaft member included in the intramedullary rod. Examples of suitable configurations include circular, splined, and other configurations. In the illustrated example, the circumferential wall 164 is circular and smooth, such that cavity 162 has a cylindrical form.

The body 142 of the head member 124 has an outer surface 170 that defines a first opening 172 on a first axial side of the body 142 and a second opening 174 positioned a second, opposite axial side of the body 142. A passageway 176 extends from the first opening 172 to the second opening 174. As best illustrated in FIGS. 2 and 5, the passageway 176 extends along an axis 178 that is disposed at a transverse angle to the first longitudinal axis 110 of the intramedullary rod 100. The passageway 176 is sized and configured to receive a lag screw used for securing the intramedullary rod 100 to a bone.

The head extension 130 is disposed about the first end 138 of the head member 124 and includes a wall 180 that defines the terminal surface 182 on, the first end 102 of the intramedullary rod 100 and a second end 183 that interfaces with the circumferential shoulder 154, as described in more detail herein. Also, the head extension 130 defines head extension lumen 184 that is in communication with the head member lumen 148. As best, illustrated in FIG. 2, the wall 180 of the head extension 130 has a wall width 186 that is substantially the same as the radial width 157 of the circumferential shoulder 154 of the head member 124. Each of the head extension 130 and the head member 124 defines structure that facilitates formation of an interface between the head member 124 and the head extension 130 such that they are attached to one another (e.g., permanently). As best illustrated in FIG. 1, this structural arrangement forms a circumferential interface 188 between the head extension 130 and the head member 124 that is smooth and effectively seamless. In alternative embodiments, a head extension 130 can be conical (e.g., include a taper between about 1 degree and about 5 degrees).

The head member 124 is advantageously formed of a metal. As such, the head member 124, and specifically the circumferential flange 150, provides a surface suitable for receiving a force, such as a hammering force transmitted to the head member 124 while the intramedullary rod is attached to a targeting device, as described in detail below. Examples of suitable metals for the head member 124 include, but are not limited to, Titanium, Magnesium, and other metals. Importantly, by placing the circumferential flange 150 away from the terminal surface 182 of the first end 102 of the intramedullary rod 100, the head extension 130 need not be adapted for receiving such force. As a result, the head extension 130 can be formed of materials that are relatively weaker than the material of the head member 124. This can be advantageous, and is indeed preferred, as it allows the head extension 130 to be formed of a material that provides other performance characteristics to the first end 102 of the intramedullary rod. For example, the head extension 130 can be formed of a radiolucent material, which may be beneficial when evaluating positioning of the intramedullary rod 100 during placement in a bone. Examples of suitable radiolucent materials include, but are not limited to, polyether ether ketone (PEEK), carbon fiber reinforced polymers, and other polymeric materials.

The shaft member 126 has a first end 190, a second end 192, and a body 194 extending between the first end 190 and the second end 192. The shaft member 126 defines a shaft member lumen 196 that extends from the first end 190 to the second end 192. Thus, the shaft member 126 is a tubular member. In the assembled intramedullary rod 100, the first end 190 is disposed within the cavity 162 of the head member 124 in a manner that places the shaft member lumen 196 in communication with the head member lumen 148 defined by the head member 124.

The shaft member 126 has an outer surface 198. As described in detail below, the outer body member 128 circumferentially surrounds the shaft member 126 and is in contact with the outer surface 198. The outer surface 198 can be treated in a manner that prepares the shaft member 126 for bonding, contact, or other interface with the outer body member 128. If a surface treatment is included, any suitable surface treatment can be used and a skilled artisan will be able to select a suitable surface treatment for an intramedullary rod according to a particular embodiment based on various considerations, such as the materials of the head member and shaft member of the intramedullary rod. Examples of suitable surface treatments include roughening, etching, and other surface treatments. Also, the portion of the outer surface on the first end of the shaft member can be left untreated or treated in a different manlier than the remainder of the shaft member in an intramedullary rod according to a particular embodiment if desirable or necessary, such as to facilitate formation of a head-shaft assembly.

In the illustrated embodiment, the shaft member 126 is a separate member that extends from the head member 124 and that is partially disposed within the head member 124. It is noted, though, that, in some embodiments, the shaft member and the head member can be formed as a single structural member. In these embodiments, the head member and shaft member each define structural portions of a single structural member. It is noted, though, that the inclusion of separate members is considered advantageous at least because it imparts modularity onto the intramedullary rod, which provides an opportunity to realize efficiencies in the manufacturing of many intramedullary rods, particularly when manufacturing intramedullary rods according to multiple embodiments having shaft members with different axial lengths but similar head members, such as the intramedullary rod 100 illustrated in FIG. 1 and the intramedullary rod 300 illustrated in FIG. 7.

The outer body member 128 is a tubular member disposed circumferentially around the shaft member 126 and extension 160 of the head member 124. Similar to the head extension 130, the outer body member 128 can be formed of materials that are relatively weaker than the material of the head member 124. Indeed, it is considered advantageous to form the outer body member 128 of the same material as the head extension. Thus, the outer body member 128 can be formed of a radiolucent material, such as polyether ether ketone (PEEK), carbon fiber reinforced polymers, and other polymeric materials. It is noted, though, that the outer body member 128 can be formed of a material that is different than the material of the head extension 130.

Each of the shaft member and outer body member in an intramedullary rod according to an embodiment can have any suitable configuration and a skilled artisan will be able to select an appropriate configuration for each of these elements for a particular embodiment based on various considerations, including the nature of the medullary canal of the bone or bone type with which the intramedullary rod is intended to be used. Each of the shaft member and outer body member in an intramedullary rod according to an embodiment can have any outer diameter. Furthermore, the shaft member and outer body member in an intramedullary rod according to an embodiment can have any suitable relative outer diameters. A skilled artisan will be able to select suitable outer diameters, and relative outer diameters, for the shaft member and outer body member in an intramedullary rod according to a particular embodiment based on various considerations, including the nature of the bone with which the intramedullary rod is intended to be used, the nature of the materials used for the shaft member and the outer body member, and other considerations. The outer diameters, and relative outer diameters, illustrated herein provide examples of outer diameters and relative outer diameters considered suitable for intramedullary rods. An intramedullary rod can be configured to be positioned within any suitable portion of a body. For example, the intramedullary rods described herein can comprise a hip fracture intramedullary rod, a proximal tibia intramedullary rod, a proximal humeral intramedullary rod, a humeral intramedullary rod, a proximal femur intramedullary rod, distal femur intramedullary rod, TTC intramedullary rod, and any other intramedullary rod considered suitable for a particular embodiment.

In the illustrated embodiment, the intramedullary rod 100 defines a locking screw passageway 155 that extends from one side of the intramedullary rod 100 to the opposite side of the intramedullary rod 100. The locking screw passageway 155 is sized and configured for receiving a locking screw commonly used in the stabilization and fixation of bone fractures, such as hip fractures. While optional, inclusion of locking screw passageways is considered advantageous to facilitate securement of the intramedullary rod 100 to bone during placement. Also, any suitable number of locking screw passageways can be included in an intramedullary rod according to a particular embodiment and a skilled artisan will be able to select an appropriate number of locking screw passageways for a particular embodiment based on various considerations, including any number of locking screws considered desirable or potentially necessary for use of the intramedullary rod in stabilization and/or fixation of a particular bone fractures. Furthermore, while the illustrated locking screw passageway 155 is positioned such that it extends through the head member 124, a locking, screw passageway in an intramedullary rod according to a particular embodiment can be located at any suitable position along the length of the intramedullary rod.

Figure 3:
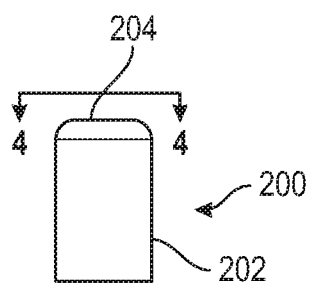
FIG. 3 is a side view of an example cap.
Figure 4:
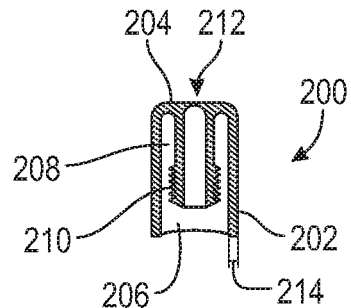
FIG. 4 is sectional view of the cap illustrated in FIG. 3, taken along line 4-4 in FIG. 3.

FIGS. 3 and 4 illustrates a cap 200 suitable for use with intramedullary rod 100. While the cap 200 is optional, it is considered advantageous as it provides a continuous outer surface, effectively eliminating the circumferential shoulder 150 from the outer profile of the intramedullary rod 100. As such, the cap 200 can be installed onto the head extension 130 after the intramedullary rod 100 has been placed in a bone. That is, the cap 200 can be installed onto the head extension 130 after the circumferential shoulder 150 has been used to accept a force from a targeting device during placement of the intramedullary rod 100. After placement, the circumferential shoulder 150 still defines a step on the outer surface of the intramedullary rod 100 and, if this is undesirable for any reason, the cap 200 can be installed to eliminate the step.

The cap 200 includes a circumferential wall 202 and an end wall 204 that cooperatively define an interior chamber 206. A projection 208 extends from the inner surface of the end wall 204 into the interior chamber 206. The projection 208 defines an outer threaded surface 210 configured to matingly engage with threaded wall 158 of head member 124. A cap passageway 212 extends through the cap 200 and, as best illustrated in FIG. 5, is continuous with passageway 156. The circumferential wall 202 has a wall thickness 214 that is equal to the radial width of the circumferential flange 150 of the head member 124.

If included, cap 200 can be formed of any suitable material, including metals and non-metals. It is considered advantageous to form the cap of the same material from which the head extension 130 is formed as this effectively preserves the advantages provided by the head extension 130 when the cap 200 is installed. As a result, the cap 200 can be formed of materials that are relatively weaker than the material of the head member 124, including radiolucent materials such as, polyether ether ketone (PEEK), carbon fiber reinforced polymers, and other polymeric materials.

Figures 6, 6A:
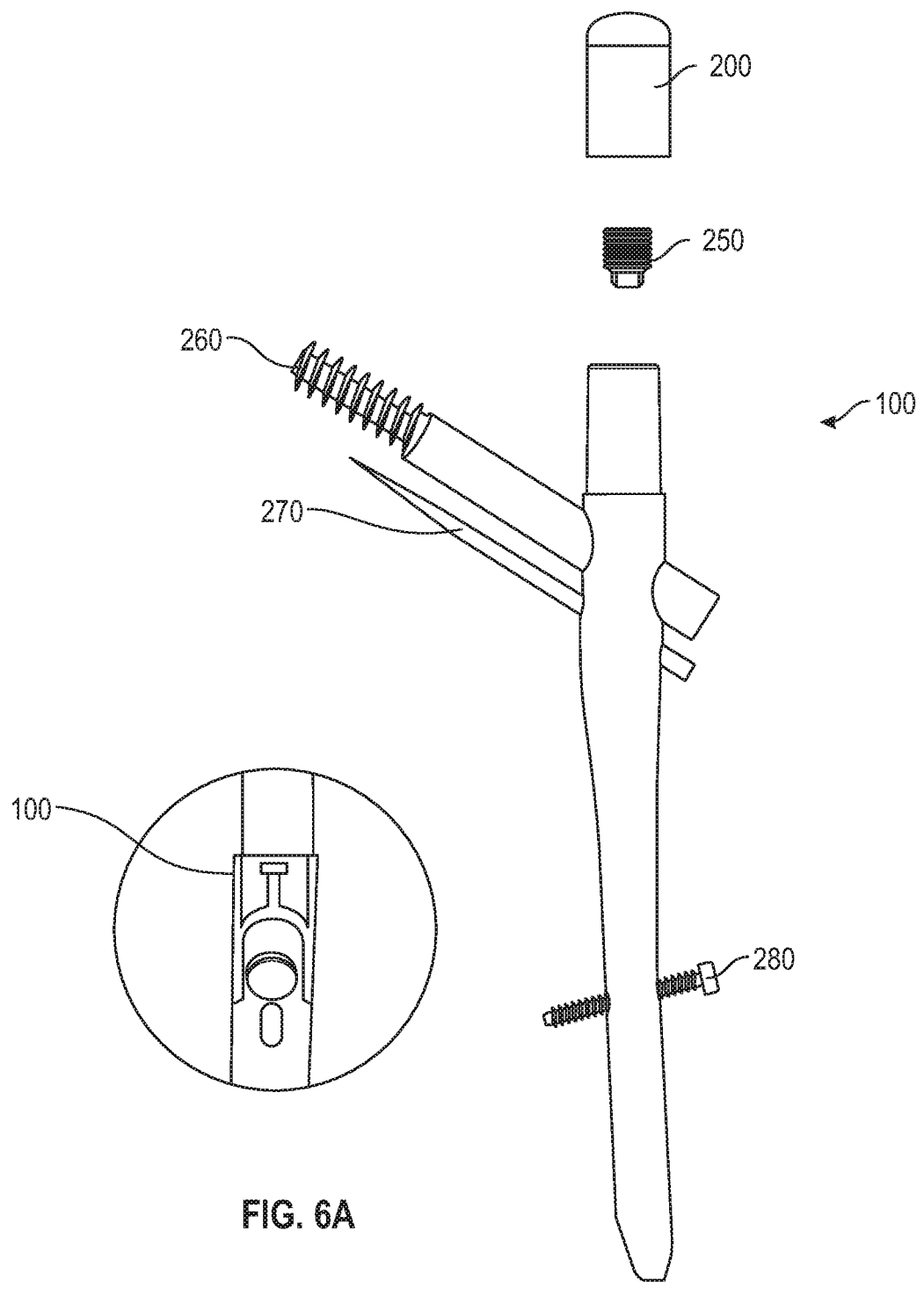
FIG. 6 is an exploded view of the intramedullary rod illustrated in FIG. 1 with the cap illustrated in FIG. 3 and a cannulated set screw, along with a lag screw, an anti-rotation, pin, and a locking screw.
FIG. 6A is a magnified view of a portion of the side of the intramedullary rod illustrated in FIG. 6.

FIG. 6 illustrates intramedullary rod 100 illustrated in FIG. 1 with the cap 200 illustrated in FIG. 3 and a cannulated set screw 250, along with a lag screw 260, an anti-rotation pin 270, and a locking screw 280 in interface with the intramedullary rod 100.

As best illustrated in FIG. 6A, the outer body member 128 in the illustrated embodiment is extends around the first opening 172 on the body 142 of the head member 124. This placement of the outer body member 128 protects the intramedullary rod 100 from damage the could be imparted on the intramedullary rod 100 during placement of a lag screw, either by interaction with the lag screw or with an accessory used in placement of the lag screw, such as a drill.

Figure 7:
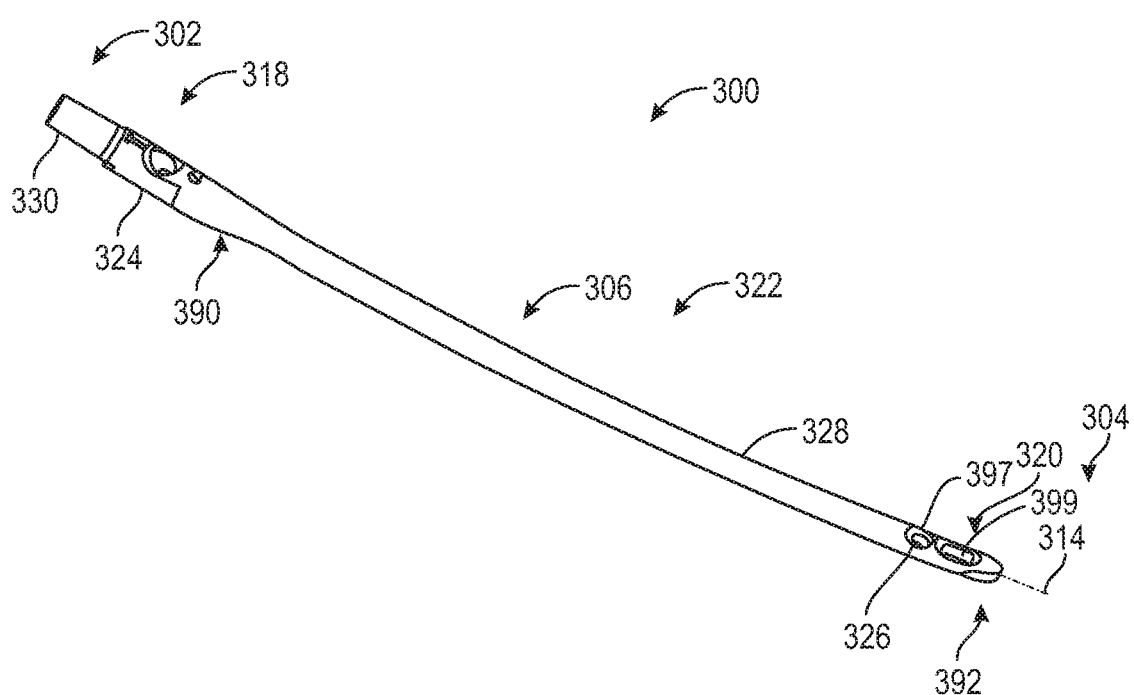
FIG. 7 is a perspective view of another example intramedullary rod.

FIG. 7 illustrates another intramedullary rod 300. The intramedullary rod 300 is similar to the intramedullary rod 100 described above and illustrated in FIGS. 1, 2, and 5, except as detailed below. Thus, the intramedullary rod 300 has a first end 302, a second end 304, and a body 306 extending between the first end 302 and the second end 304. The intramedullary rod 300 includes a head portion 318 that includes the first end 302, a tip portion 320 that includes the second end 304, and a shaft portion 322 extending between the head portion 318 and the tip portion 320 and comprising the body 306. Also, the intramedullary rod 300 includes a head member 324, a shaft member 326 partially disposed within the head member 324, an outer body member 328 disposed circumferentially around the shaft member 326 and a portion of the head member 324, and a head extension 330 disposed on a portion of the head member 324 and extending away from the second end 304 of the intramedullary rod 300 to the first end 302 of the intramedullary rod 300.

In the illustrated embodiment, the shaft member 326 has an axial length that is greater than the axial length of the shaft member 126 illustrated in FIGS. 1, 2, and 5. In addition, the shaft member 326 and the outer body member 328 cooperatively define two passageways 397, 399 between the first end 390 and the second end 392 of the shaft member 326. Each of the passageways 397, 399 extends along an axis that is disposed at a transverse angle to the second longitudinal axis 314 of the intramedullary rod 300. Each of the passageways 397, 399 is sized and configured to receive a lag screw used for securing the intramedullary rod 300 to a bone. In the illustrated embodiment, the second passageway 399 is elongated and has a length along the second longitudinal axis 314 that is greater than the length of the first passageway 397 along the second longitudinal axis 314.

A shaft member included in an intramedullary rod can have any suitable axial length and selection of a suitable axial length can be based on various considerations, including the intended use of the intramedullary rod. Examples of axial lengths considered suitable for a shaft member include lengths that are equal to, greater than, less than, or about the axial length of a head member, axial lengths that are two times the axial length of a head member, axial lengths that are three times the axial length of a head member, axial lengths that are four times the axial length of a head member, axial lengths that are greater than four times the axial length of a head member, and any other length considered suitable for a particular embodiment. While intramedullary rod 300 has been illustrated as defining two passageways 397, 399 between the first end 390 and the second end 392 of the shaft member 326, an intramedullary rod can define any suitable number of passageways between a first end and a second end of a shaft member and each passageway can have any suitable configuration. Examples of numbers of passageways considered suitable for an intramedullary rod to define include one, more than one, two, a plurality, three, four, five, and any other number considered suitable for a particular embodiment.

Figure 8:
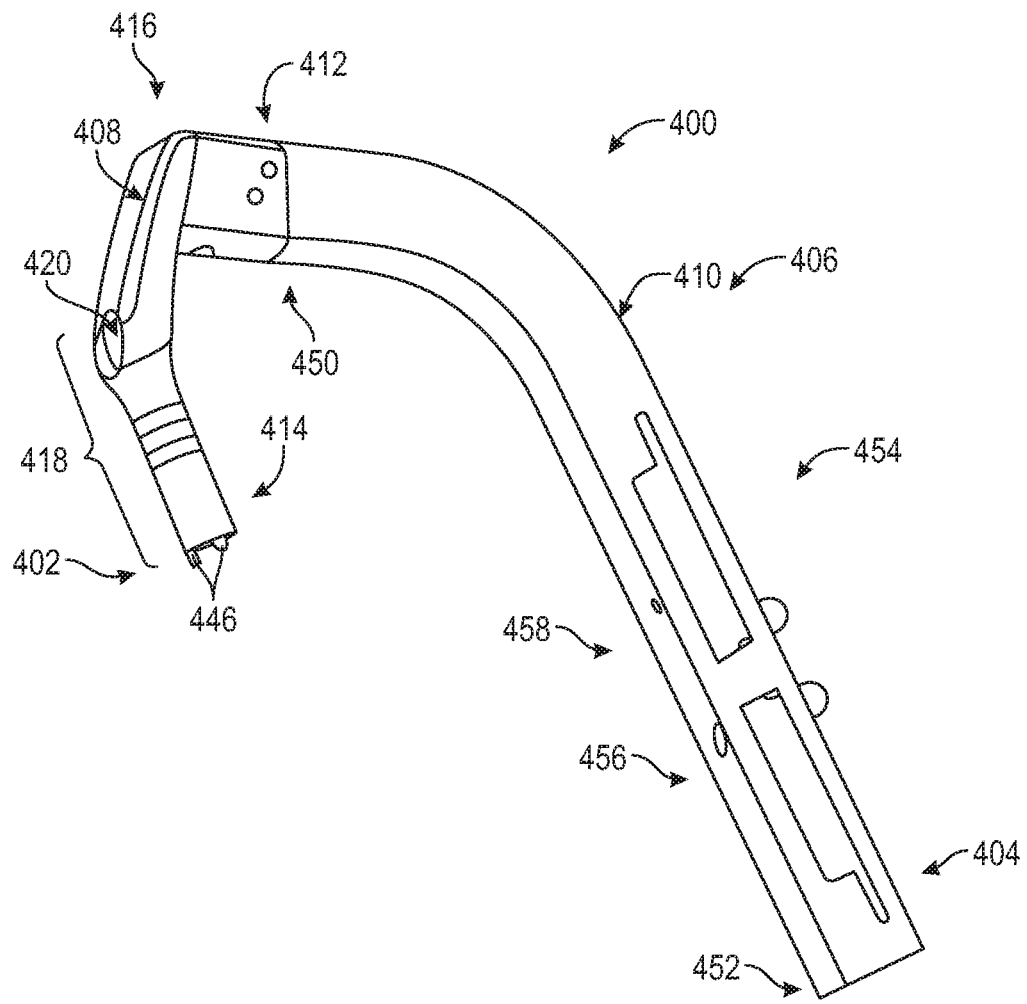
FIG. 8 is a perspective view of an example targeting device.
Figure 9:
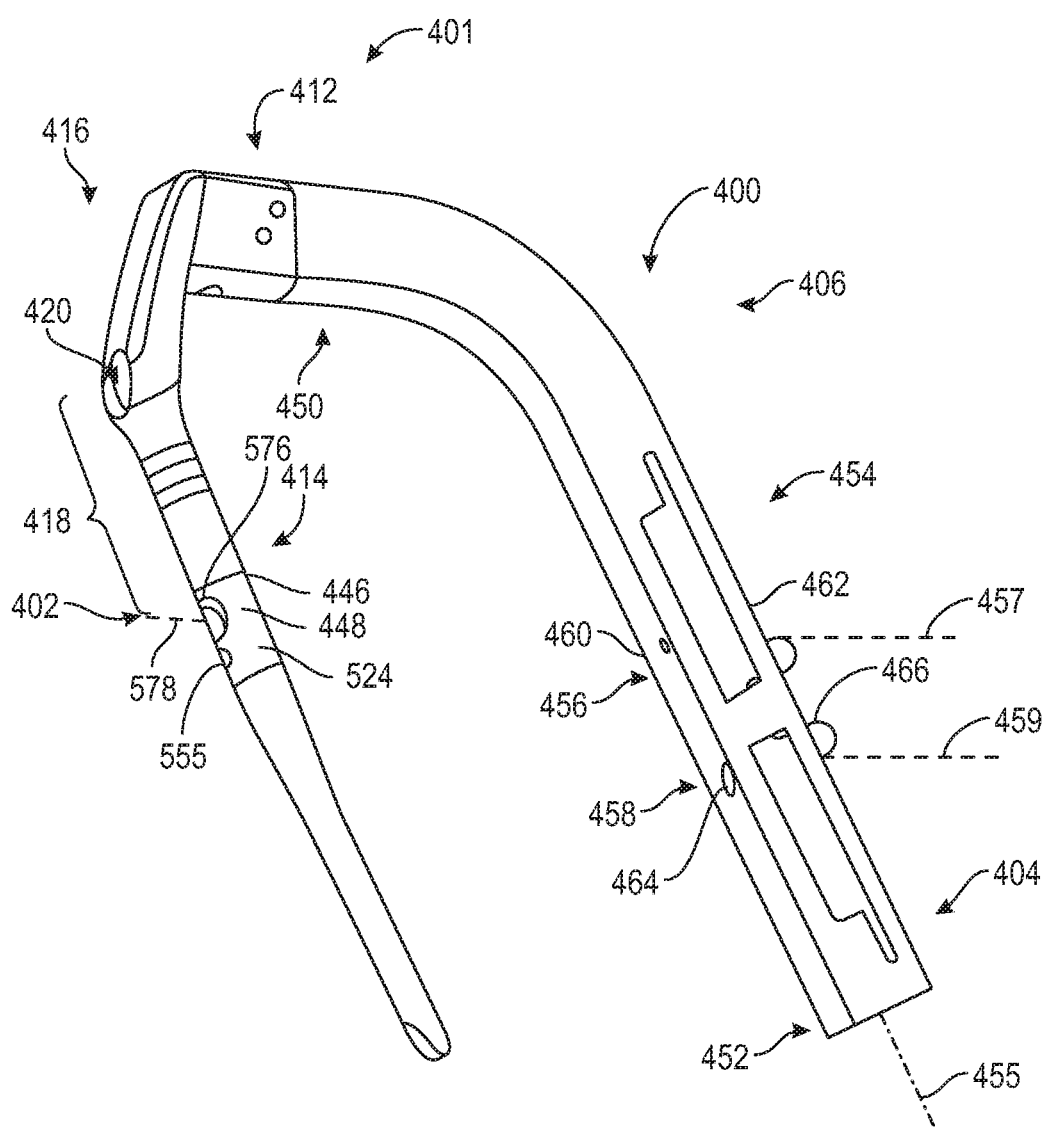
FIG. 9. is a perspective view of an example intramedullary rod system.

FIG. 8 illustrates an example targeting device 400. FIGS. 8 and 9 illustrate the targeting device 400 illustrated in FIG. 8 attached to an intramedullary rod 500 creating an intramedullary rod system 401. The intramedullary rod 500 is similar to the intramedullary rod 500 described above and illustrated in FIGS. 1, 2, and 5, except as detailed below. The targeting device 400 has a first end 402, a second end 404, and a body 406 extending between the first end 402 and the second end 404. The targeting device 400 includes a rod engaging member 408 that includes the first end 402 and a handle 410 that includes the second end 404.

The rod engaging member 408 has a first end 412, a second end 414, and a body 416 that extends from the first end 412 to the second end 414. The rod engaging member 408 defines structure on the first end 412 that interfaces with the handle 410 such that attachment to the handle 410 can be accomplished. The rod engaging member 408 defines a rod engaging sleeve 418 that has a rod engaging lumen 420. The rod engaging sleeve 418 has a first end 422, a second end 424, a first portion 426, a second portion 428, and a third portion 430. The first portion 426 extends from the first end 422 toward the second end 424 and has a first wall width 425. The second portion 428 is disposed between the first and third portions 426, 430 and has a second wall width 429. The third portion 430 extends from the second portion 428 to the second end 424 and has a third wall width 431. The first wall width 425 and the third wall width 431 are each less than the second wall width 429. The third wall width 431 is equal to, or substantially the same as, the radial width 552 the circumferential flange 550. The rod engaging sleeve 418 provides structure for interfacing with an intramedullary rod, such as an intramedullary rod according to an embodiment described herein. For example, the rod engaging sleeve 418 defines a second end 424, which cooperates with a head extension and a head member of an intramedullary rod to interface with an intramedullary rod, as described in detail below.

The rod engaging lumen 420 extends from a first opening 432 defined between the first, and second ends 412, 414 of the rod engaging member 408 to a second opening 434 defined on the second end 414 of the rod engaging member 408. The rod engaging member lumen 420 extends along an axis 421 that extends through each of the first opening 432 and the second opening 434. The rod engaging lumen 420 has a first portion 436, a second portion 438, and a third portion 440. The first portion 436 has a first inside diameter 437, the second portion 438 has a second inside diameter 439, and the third portion 440 has a third inside diameter 441. The second inside diameter 439 is less than the first inside diameter 437 and the third inside diameter 441 such that a first shoulder 442 and a second shoulder 444 are defined within the rod engaging lumen 420.

Figure 10:
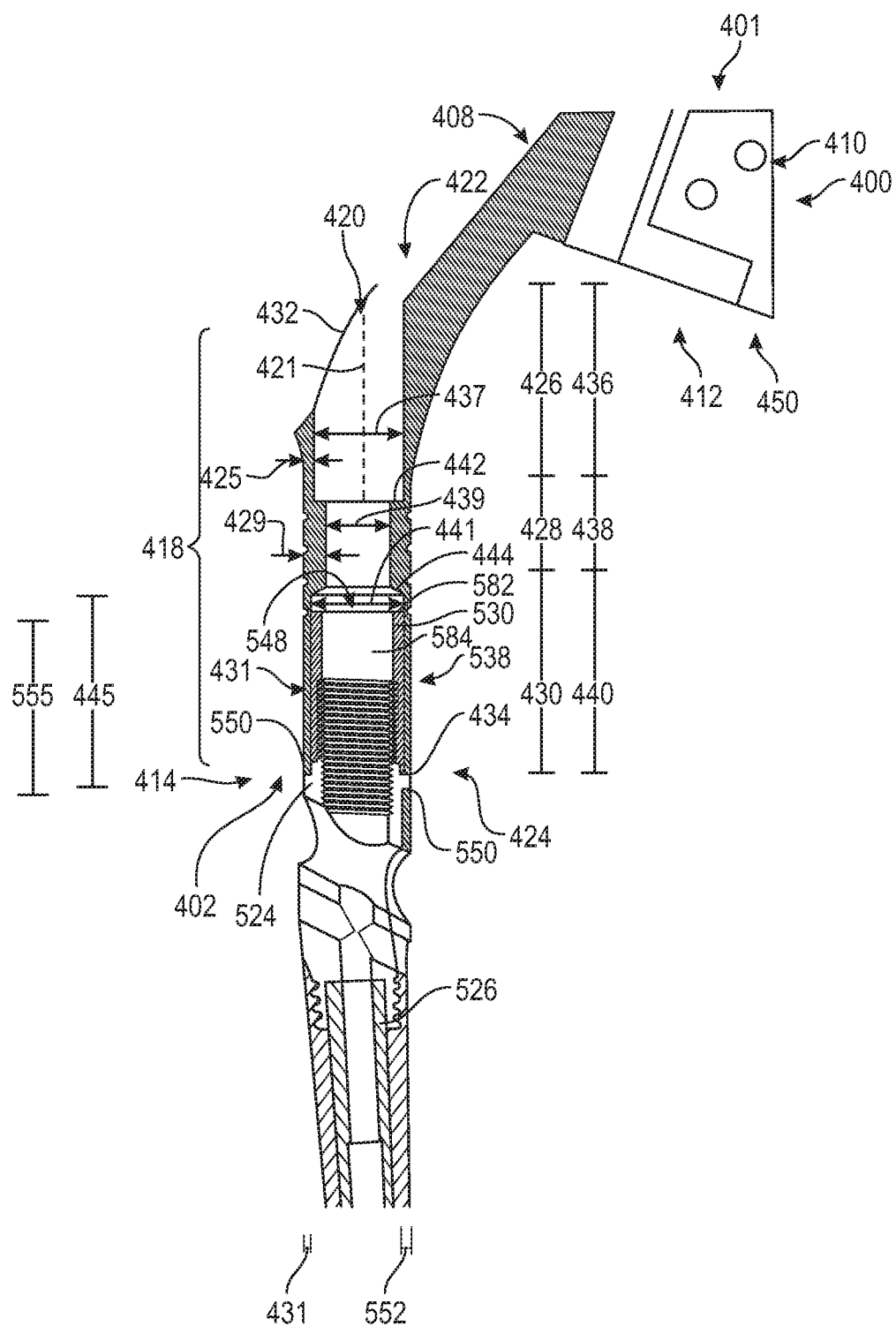
FIG. 10 is a partial sectional view of the intramedullary rod system illustrated in FIG. 9.

As shown in FIG. 10, the first end 538 of the head member 524 is disposed within the rod engaging lumen 420 when the intramedullary rod 500 is attached to the targeting device 400 such that the rod engaging lumen 420 is in line with the head member lumen 548. In use, the rod engaging member 408 and the intramedullary rod 500 can be passed over a previously-placed wire such that the wire extends through the rod engaging lumen 420, the shaft member 526, the head member lumen 548 and, ultimately, through the head extension lumen 584 if desired or necessary. In this manner, the targeting device 400 and the intramedullary rod 500 can then be advanced over the wire to a desired degree to achieve a desired placement and/or positioning before securing the intramedullary rod 500 within the medullary canal.

The second shoulder 444 is positioned a distance 445 from the second end 414 that is greater than the distance 555 from the terminal surface 582 of the head extension 530 and the circumferential flange 550 such that when the intramedullary rod 500 is disposed within the targeting device 400 the terminal surface 582 of the head extension 530 does not contact the second shoulder 444. Rather, the rod engaging member 408 provides a surface for forming a contact interface with an intramedullary rod. As shown in FIG. 10, the second end 424 of the rod engaging sleeve 418 contacts the circumferential flange 550 of the head member 524 such that the terminal end 582 of the of the head extension 530 is disposed within the rod engaging lumen 420. The rod engaging member 408 is advantageously formed of a metal (e.g., titanium). As such, the rod engaging member 408, and specifically the rod engaging sleeve 418, provides a surface (e.g., second end 424 of the rod engaging sleeve 418) suitable for transferring a force, such as a hammering force, to the head member 524 (e.g., circumferential flange 550) while the intramedullary rod 500 is attached to the targeting device 400. The interaction, between the rod engaging sleeve 418 and the circumferential flange 550 prevents contact between the terminal surface 582 of the head extension 530 and the rod engaging member 408.

As shown in FIGS. 8 and 9, the rod engaging member 408 defines a plurality of projections 446 that extend from the second end 414 of the rod engaging member 408 and away from the first end 412 of the rod engaging member 408. Each projection of the plurality of projections 446 defines structure that interfaces with a recess of a plurality of recesses 448 defined by the head member 524 disposed within the targeting device 400 to provide rotational strength between the targeting device 400 and the intramedullary rod 500.

While the rod engaging member 408 has been illustrated as defining a rod engaging lumen 420, alternative rod engaging members can define a recess that extends from the second end of the rod engaging member toward the first end of the rod engaging member to a recess base and that includes structure similar to the second portion 438 and/or third portion 440 of the rod engaging member lumen 420 illustrated herein.

The handle 410 has a first end 450, a second end 452, and a body 454 that extends from the first end 450 to the second end 452. The handle 410 defines structure on the first end 450 that interfaces with the rod engaging member 408 such that attachment to the rod engaging member 408 can be accomplished. The handle 410 also defines a first passageway 456 and a second passageway 458. The first passageway 456 extends from a first opening 460 to a second opening 462 and, the second passageway 458 extends from a first opening 464 to a second opening 466. As best illustrated in FIG. 10, when the intramedullary rod 500 is attached to the targeting device 400, the first passageway 456 extends along an axis 457 that is disposed at a transverse angle to the longitudinal axis 455 of the handle 410 and is coaxial with the axis 578 that extends through passageway 576 defined by the head member 524. The first passageway 456 is sized and configured to assist with positioning a lag screw through passageway 576 that is used for securing the intramedullary rod 500 to a bone. As best illustrated in FIG. 10, the second passageway 458 extends along an axis 459 that is disposed at a transverse angle to the longitudinal axis 455 of the handle 410 and is coaxial with the axis that extends through the locking screw passageway 555 defined by the head member 524. The second passageway 458 is sized and configured to assist with positioning a locking screw through locking screw passageway 555.

While intramedullary rod system 401 has been illustrated as including targeting system 400 and intramedullary rod 500, an intramedullary rod system can include any suitable targeting system and intramedullary rod. Selection of a suitable targeting system and intramedullary rod to include in an intramedullary rod system can be based on various considerations, including the intended use of the intramedullary rod system.

Figure 11:
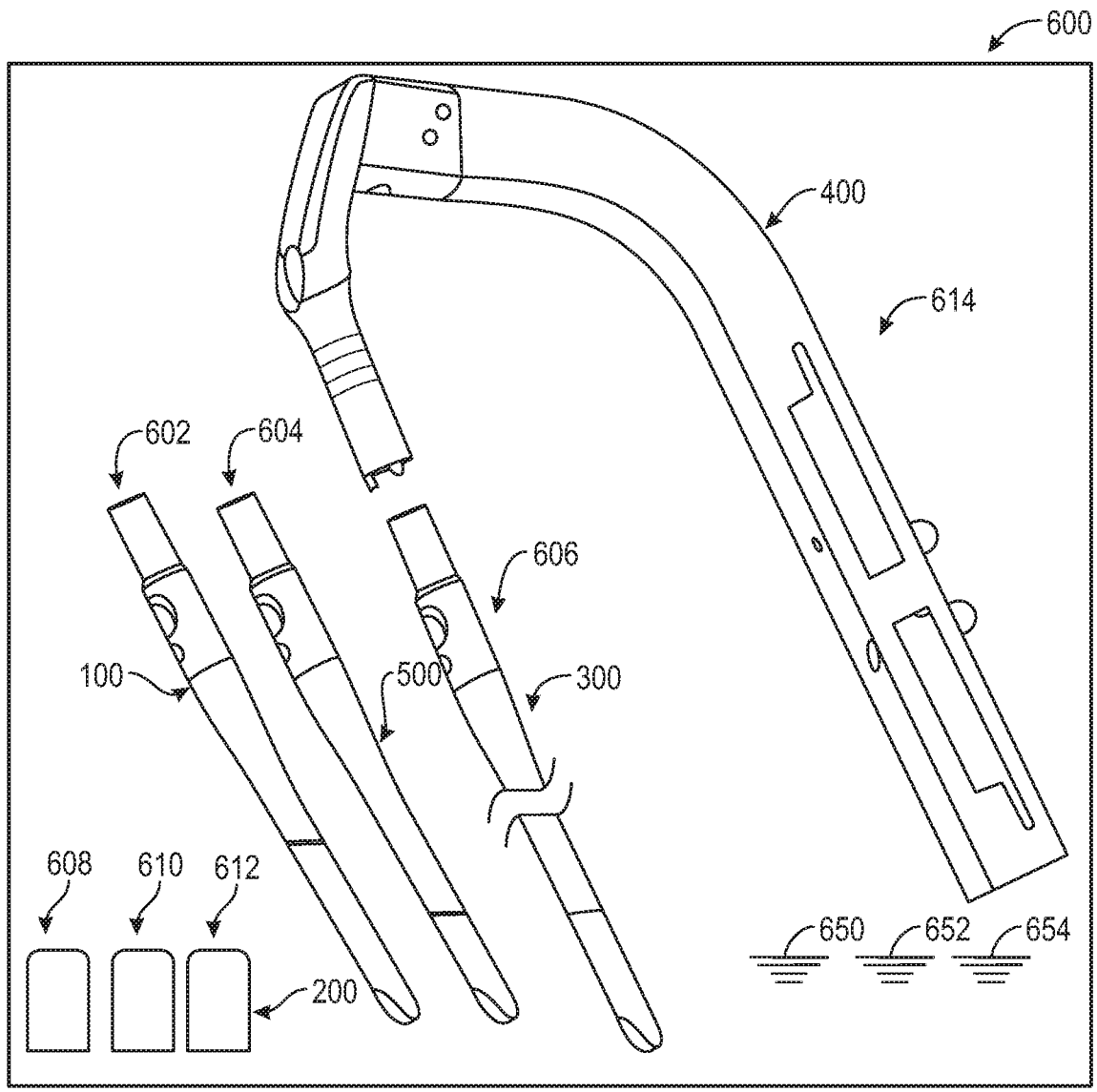
FIG. 11 is a schematic representation of an example intramedullary rod kit.

FIG. 11 illustrates a schematic representation of an example intramedullary rod kit 600. The intramedullary rod kit 600 includes a first intramedullary rod 602 according to an embodiment, a second intramedullary rod 604 according to an embodiment, a third intramedullary rod 606 according to an embodiment, a first cap 608 according to an embodiment, a second cap 610 according to an embodiment, a third cap 612 according to an embodiment, and a targeting device 614 according to an embodiment. In this example, the intramedullary rod kit 600 also includes a first cannulated set screw 650, a second cannulated set screw 652, and a third cannulated set screw 654.

Any suitable intramedullary rod, cap, and targeting device can be included in a kit and selection of a suitable intramedullary rod, cap, and targeting device to include in a kit can be based on various considerations, including the procedure intended to be performed using the kit. Examples of intramedullary rods considered suitable to include in a kit include intramedullary rod 100, intramedullary rod 300, intramedullary rod 500, variations of the intramedullary rods described herein, and any other intramedullary rod according to an embodiment. Examples of caps considered suitable to include in a kit, include cap 200, variations of the caps described herein, and any other cap according to an embodiment. Examples of targeting devices considered suitable to include in a kit include targeting device 400, variations of the targeting devices described herein, and any other targeting device according to an embodiment. Optionally, a kit can include an intramedullary system, such as intramedullary system 401. In the illustrated embodiment, the kit 600 includes intramedullary rod 100, as shown in FIGS. 1, 2, and 5, intramedullary rod 300, as shown in FIG. 7, intramedullary rod 500, as shown in FIGS. 8 and 9, three caps 200, as shown in FIGS. 3 and 4, and targeting device 400, as shown in FIGS. 7, 8, and 9.

While the kit 600 has been illustrated as including three intramedullary rods 602, 604, 606, three caps 608, 610, 612, and a single targeting device 614, any suitable number, and type, of intramedullary rods, caps, and/or targeting devices can be included in a kit, such as those described herein. Selection of a suitable number of intramedullary rods, caps, and/or targeting devices to include in a kit according to a particular embodiment can be based on various considerations, such as the type of procedure intended to be accomplished using the kit. Examples of suitable numbers of intramedullary rods, caps, and/or targeting devices to include in a kit include at least one, one, two, a plurality, three, four and any other number considered suitable for a particular embodiment.

While the kit 600 has been illustrated as including only three intramedullary rods 602, 604, 606, three caps 608, 610, 612, and a single targeting device 614, a kit can include any suitable number of optional components. Examples of numbers of optional components considered suitable to include in a kit include one, at least one, two, a plurality, three, four, five, more than five, and any other number considered suitable for a particular embodiment. Examples of optional components considered suitable to include in a kit include wires for guiding an intramedullary rod and/or targeting device to a point of treatment, lag screws, anti-rotation pins, locking screws, intramedullary rod systems, and/or any other component considered suitable for a particular embodiment.

Figure 12:
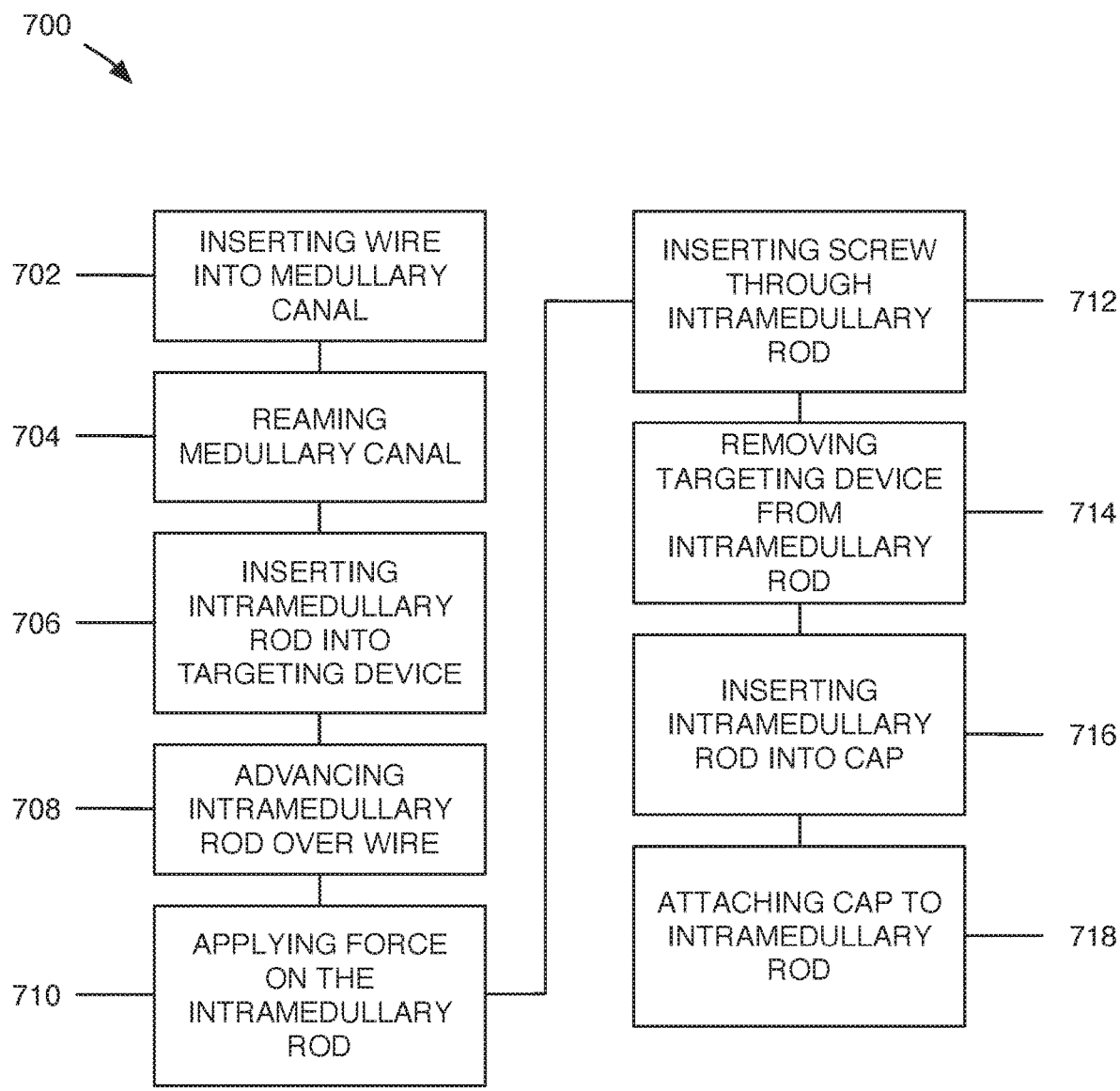
FIG. 12 is a flowchart representation of an example method of placing an intramedullary rod in a bone.

FIG. 12 is a flowchart representation of an example method 700 of placing an intramedullary rod in a bone.

A step 702 comprises inserting a wire into a medullary canal. Another step 704 comprises reaming the medullary canal. Another step 706 comprises inserting, a portion of an intramedullary rod into a targeting device. Another step 708 comprises advancing the intramedullary rod over the wire until a portion of the intramedullary rod is disposed within the medullary canal. Another step 710 comprises applying a force on the intramedullary rod directed toward the medullary canal such that the intramedullary rod is advanced into the medullary canal. Another step 712 comprises inserting a screw through the intramedullary rod. Another step 714 comprises removing the targeting device from the intramedullary rod. Another step 716 comprises inserting a portion of the intramedullary rod into a cap. Another step 718 comprises attaching the cap to the intramedullary rod.

Step 702 can be accomplished, using any suitable wire and by applying a force on the wire directed toward the medullary canal. Optionally, step 702 can be omitted from method 700.

Step 704 can be accomplished using any suitable device and by applying a force on the device directed toward the medullary canal until the device is positioned on the wire and advanced into the medullary canal. Subsequently, the device can be utilized to ream the medullary canal. Optionally, step 704 can be omitted from method 700.

Step 706 can be accomplished by inserting the head extension of an intramedullary rod into a targeting device until the second end of the rod engaging sleeve contacts the circumferential flange (e.g., circumferential flange 150) defined by the head member. This can be accomplished by applying a force on an intramedullary rod directed toward a targeting device while maintaining the position of the targeting device, or applying a second force on the targeting device directed toward the intramedullary, rod. Alternatively, step 706 can be accomplished by applying a force on a targeting device directed toward the intramedullary rod while maintaining the position of the intramedullary rod.

Step 708 can be accomplished by applying a force on the intramedullary rod and/or targeting device directed toward the medullary canal until a portion of the intramedullary rod is disposed within the medullary canal.

Step 710 can be accomplished using any suitable technique or method of applying a force on an intramedullary rod, such as using conventional hammer.

Step 712 can be accomplished using the targeting device to position a screw (e.g., lag screw) through a passageway (e.g., passageway 156) defined by the intramedullary rod such that the intramedullary rod is attached to a bone.

Step 714 can be accomplished by applying a force on the targeting device directed away from the intramedullary rod until the targeting device is free of the intramedullary rod.

Step 716 can be accomplished by inserting the head extension of an intramedullary rod into a cap until the second end of the cap contacts the circumferential flange (e.g., circumferential flange 150) defined by the head member. This can be accomplished by applying a force on a cap directed toward an intramedullary rod while maintaining the position of the intramedullary rod, or applying a second force on the intramedullary rod directed toward the cap.

Step 718 can be accomplished using any suitable technique or method of attaching a cap to an intramedullary rod, such as by applying a rotational force on the cap, such that the threads defined by the cap interface with the threads defined by the head member of the intramedullary rod.

A head member, a shaft member, a targeting member, and portions thereof, can be made of any material suitable for use in medical devices intended for orthopedic use, including use as a long-term implant. Examples of suitable materials include metals, metal alloys, and polymeric materials.

Examples of suitable metals include, but are not limited to, Titanium, Magnesium, and other metals. Examples of suitable metal alloys include, but are not limited to, Ti6Al4V, 316 LVM, 1.4441Ti-13Nb-13Zr, Ti-12Mo-6Zr-2Fe, Ti-15 bio-57r-3Al, Ti-15Mo, Ti-35Nb-7Zr-5Ta and Ti-29Nb-13Ta-4.6Zr Ti-6Al-7Nb and Ti-15Sn-4Nb-2Ta-0.2Pd Co—Cr—Mo alloys. Examples of suitable polymeric materials include, but are not limited to, polyaryletherketone (PAEK), polyether ether ketone (PEEK), PEEK (90G, 450G, I2, I4), Polyamid, PA66, carbon fiber reinforced polyaryletherketone (CFR PAEK), polyether ketone ketone (PEKK), carbon fiber reinforced polyether ketone ketone (CFR PEKK), carbon fiber reinforced polyether ether ketone (CFR PEEK), CFR PEEK (90G CA30, 90G CA20, 450G CA30, 450G CA20, I2 CF20, I2 CF30, I4 CF30, I4 CF20) Polyamid CFR, and PA66 CFR.

Those with ordinary skill in the art will appreciate that various modifications and alternatives for the described and illustrated examples can be developed in light of the overall teachings of the disclosure, and that the various elements and features of one example described and illustrated herein can be combined with various elements and features of another example without departing from the scope of the invention. Accordingly, the particular examples disclosed herein have been selected by the inventors simply, to describe and illustrate examples of the invention and are not intended to limit the scope of the invention or its protection, which is to be given the full breadth of the appended claims and any and all equivalents thereof.

We claim:

1. An intramedullary rod having a longitudinal axis, the intramedullary rod comprising:
   a head member having a first end, a second end, and a body extending between the first end of the head member and the second end of the head member, the head member formed of a first material and defining a circumferential flange and a circumferential shoulder, the circumferential flange extending radially outwardly from the head member and lying on a plane extending through the longitudinal axis of said intramedullary rod, the circumferential shoulder disposed between the first end of the head member and the circumferential flange;
   a shaft member extending from the head member, the shaft member having a first end, a second end, and a body extending between the first end of the shaft member and the second end of the shaft member; and
   a head extension partially disposed over the head member and having a wall defining a first end defining a terminal surface of said intramedullary rod and a second end that interfaces with the circumferential shoulder, the head extension formed of a second material that is different than the first material, the second end of the head extension contacting the circumferential shoulder of the head member.

2. The intramedullary rod of claim 1, wherein the shaft member comprises a separate member partially disposed within the head member.

3. The intramedullary rod of claim 2, further comprising an outer body member disposed circumferentially about the shaft member and a portion of the head member.

4. The intramedullary rod of claim 3, wherein the shaft member is formed of a metal.

5. The intramedullary rod of claim 4, wherein the outer body member is formed of a radiolucent material.

6. The intramedullary rod of claim 5, wherein the radiolucent material is PEEK.

7. The intramedullary rod of claim 6, wherein the radiolucent material is carbon fiber reinforced PEEK.

8. The intramedullary rod of claim 5, wherein the radiolucent material is a polymer.

9. The intramedullary rod of claim 1, wherein the circumferential shoulder has a radial width; and
   wherein the wall has a wall thickness that is equal to the radial width.

10. The intramedullary rod of claim 1, wherein the plane extends orthogonally through the longitudinal axis of said intramedullary rod.

11. The intramedullary rod of claim 1, wherein the circumferential shoulder is radially inward of the circumferential flange.

12. The intramedullary rod of claim 1, wherein the head extension is formed of a radiolucent material.

13. The intramedullary rod of claim 12, wherein the radiolucent material is PEEK.

14. The intramedullary rod of claim 13, wherein the radiolucent material is carbon fiber reinforced PEEK.

15. The intramedullary rod of claim 1, wherein the head member is formed of a metal.

16. The intramedullary rod of claim 1, wherein the shaft member is formed of a metal.

17. The intramedullary rod of claim 1, wherein the head member defines a lumen extending through the head member;
   wherein the shaft member defines a lumen extending through the shaft member; and
   wherein the head extension defines an extension lumen extending through the head extension.

18. The intramedullary rod of claim 1, further comprising a removable cap disposed on the head extension.

19. An intramedullary rod having a longitudinal axis, the intramedullary rod comprising:
   a head member having a first end, a second end, and a body extending between the first end of the head member and the second end of the head member, the head member formed of a first material and defining a circumferential flange and a circumferential shoulder, the circumferential flange extending radially outwardly from the head member and lying on a plane extending through the longitudinal axis of said intramedullary rod, the circumferential shoulder disposed between the first end of the head member and the circumferential flange, the head member further defining a first opening, a second opening, and a passageway extending through the head member from the first opening to the second opening;
   a shaft member extending from the head member, the shaft member having a first end, a second end, and a body extending between the first end of the shaft member and the second end of the shaft member;
   a head extension partially disposed over the head member and having a wall defining a first end defining a terminal surface of said intramedullary rod and a second end that interfaces with the circumferential shoulder, the head extension formed of a second material that is different than the first material, the second end of the head extension contacting the circumferential shoulder of the head member;
   an outer body member disposed circumferentially about the shaft member and a portion of the head member, a portion of the outer body member disposed around the first opening of the head member; and a removable cap disposed on the head extension, the cap having a first end in contact with the circumferential shoulder.

20. An intramedullary rod having a longitudinal axis, the intramedullary rod comprising:
- a head member having a first end, a second end, and a body extending between the first end of the head member and the second end of the head member, the head member formed of a first material and defining a circumferential flange and a circumferential shoulder, the circumferential flange extending radially outwardly from the head member and lying on a plane extending through the longitudinal axis of said intramedullary rod, the circumferential shoulder disposed between the first end of the head member and the circumferential flange, the head member further defining a first opening, a second opening, and a passageway extending through the head member from the first opening to the second opening;
- a shaft member extending from the head member, the shaft member having a first end, a second end, and a body extending between the first end of the shaft member and the second end of the shaft member;
- a head extension partially disposed over the head member and having a wall defining a first end defining a terminal surface of said intramedullary rod and a second end that interfaces with the circumferential shoulder, the head extension formed of a second material that is different than the first material, the second end of the head extension contacting the circumferential shoulder of the head member; and
- an outer body member disposed circumferentially about the shaft member and a portion of the head member, a portion of the outer body member disposed around the first opening of the head member;
- a removable cap disposed on the head extension, the cap having a first end in contact with the circumferential shoulder;
- wherein each of the head member and shaft member comprises a metal; and
- wherein each of the head extension, outer body member, and removable cap comprises a radiolucent material.

* * * * *